(12) United States Patent
Spivey et al.

(10) Patent No.: US 9,089,320 B2
(45) Date of Patent: Jul. 28, 2015

(54) METHODS AND DEVICES FOR DELIVERING AND APPLYING MULTIPLE SUTURE ANCHORS

(75) Inventors: James T. Spivey, Cincinnati, OH (US); Duane Linenkugel, Cincinnati, OH (US); Andrew M. Zwolinski, Cincinnati, OH (US); William D. Fox, New Richmond, OH (US); Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1179 days.

(21) Appl. No.: 12/237,858

(22) Filed: Sep. 25, 2008

(65) Prior Publication Data

US 2010/0076488 A1    Mar. 25, 2010

(51) Int. Cl.
*A61B 17/04* (2006.01)
*A61B 17/00* (2006.01)

(52) U.S. Cl.
CPC ..... *A61B 17/0469* (2013.01); *A61B 2017/0034* (2013.01); *A61B 2017/00278* (2013.01); *A61B 2017/00292* (2013.01); *A61B 2017/0409* (2013.01); *A61B 2017/0417* (2013.01); *A61B 2017/0454* (2013.01); *A61B 2017/0464* (2013.01)

(58) Field of Classification Search
CPC ............... A61B 2017/0409; A61B 2017/0407; A61B 2017/0417; A61B 17/0469
USPC ......... 606/139, 142, 143, 213, 232, 144, 148, 606/151, 157
See application file for complete search history.

(56) References Cited

U.S. PATENT DOCUMENTS

| | | | |
|---|---|---|---|
| 5,100,415 A | 3/1992 | Hayhurst | |
| 5,268,001 A | 12/1993 | Nicholson et al. | |
| 5,391,182 A | 2/1995 | Chin | |
| 5,507,757 A * | 4/1996 | Sauer et al. | 606/144 |
| 5,573,540 A | 11/1996 | Yoon | |
| 5,755,727 A * | 5/1998 | Kontos | 606/144 |

(Continued)

FOREIGN PATENT DOCUMENTS

| | | |
|---|---|---|
| EP | 1808134 A2 | 7/2007 |
| EP | 1938760 A1 | 7/2008 |

(Continued)

OTHER PUBLICATIONS

International Search Report; Application PCT/US2009/057408, mailed Dec. 16, 2009; 9 pages.

(Continued)

*Primary Examiner* — Alexander Orkin
(74) *Attorney, Agent, or Firm* — Mintz Levin Cohn Ferris Glovsky and Popeo, P.C.

(57) ABSTRACT

Methods and devices are provided for deploying and applying multiple suture anchors. In one embodiment, a surgical device is provided having a shaft configured to be introduced into a body, e.g., through a scoping device, and to deliver a plurality of suture anchors into tissue, preferably without the need to remove the shaft from the body. The shaft can have a plurality of channels, with each of the plurality of channels configured to seat at least one of a plurality of suture anchors. Each of the anchors can be removably seated in a channel such that the anchors can be removed from the device, such as by pulling on sutures attached to the respective anchors.

22 Claims, 9 Drawing Sheets

(56) References Cited

U.S. PATENT DOCUMENTS

| | | | |
|---|---|---|---|
| 5,810,845 A | 9/1998 | Yoon | |
| 6,117,144 A | 9/2000 | Nobles et al. | |
| 6,290,674 B1 | 9/2001 | Roue et al. | |
| 6,315,784 B1 | 11/2001 | Djurovic | |
| 6,447,524 B1 | 9/2002 | Knodel et al. | |
| 6,524,316 B1 | 2/2003 | Nicholson et al. | |
| 6,626,930 B1 | 9/2003 | Allen et al. | |
| 6,699,263 B2 | 3/2004 | Cope | |
| 6,896,685 B1 * | 5/2005 | Davenport | 606/144 |
| 6,911,034 B2 | 6/2005 | Nobles et al. | |
| 7,722,629 B2 | 5/2010 | Chambers | |
| 7,744,613 B2 | 6/2010 | Ewers et al. | |
| 7,824,382 B2 | 11/2010 | Reihl et al. | |
| 7,887,551 B2 | 2/2011 | Bojarski et al. | |
| 2002/0049453 A1 | 4/2002 | Nobles et al. | |
| 2003/0009177 A1 | 1/2003 | Middleman et al. | |
| 2003/0158562 A1 * | 8/2003 | Feigl | 606/148 |
| 2003/0195562 A1 | 10/2003 | Collier et al. | |
| 2003/0204195 A1 | 10/2003 | Keane et al. | |
| 2004/0162568 A1 | 8/2004 | Saadat et al. | |
| 2004/0186486 A1 | 9/2004 | Roue et al. | |
| 2004/0230095 A1 | 11/2004 | Stefanchik et al. | |
| 2005/0021057 A1 * | 1/2005 | St. Goar et al. | 606/144 |
| 2005/0113851 A1 | 5/2005 | Swain et al. | |
| 2005/0251205 A1 | 11/2005 | Ewers et al. | |
| 2005/0267533 A1 | 12/2005 | Gertner | |
| 2006/0025819 A1 | 2/2006 | Nobis et al. | |
| 2006/0030885 A1 | 2/2006 | Hyde | |
| 2006/0142784 A1 | 6/2006 | Kontos | |
| 2007/0005080 A1 * | 1/2007 | Wolniewicz et al. | 606/142 |
| 2007/0032823 A1 | 2/2007 | Tegg | |
| 2007/0073342 A1 | 3/2007 | Stone et al. | |
| 2007/0100348 A1 | 5/2007 | Cauthen et al. | |
| 2007/0100354 A1 * | 5/2007 | Cauthen, III et al. | 606/104 |
| 2007/0112384 A1 | 5/2007 | Conlon et al. | |
| 2007/0112385 A1 | 5/2007 | Conlon | |
| 2007/0260273 A1 | 11/2007 | Cropper et al. | |
| 2007/0270889 A1 | 11/2007 | Conlon et al. | |
| 2008/0086172 A1 | 4/2008 | Martin et al. | |
| 2008/0097483 A1 | 4/2008 | Ortiz et al. | |
| 2008/0103527 A1 | 5/2008 | Martin et al. | |
| 2008/0161850 A1 | 7/2008 | Weisenburgh et al. | |
| 2008/0275474 A1 | 11/2008 | Martin et al. | |
| 2010/0076462 A1 | 3/2010 | Bakos et al. | |
| 2010/0106166 A1 | 4/2010 | Cropper et al. | |

FOREIGN PATENT DOCUMENTS

| | | |
|---|---|---|
| FR | 2785171 A1 | 5/2000 |
| WO | WO-0222026 A1 | 3/2002 |
| WO | WO-2008137534 | 11/2008 |
| WO | WO-2008137537 | 11/2008 |

OTHER PUBLICATIONS

International Search Report, Application No. PCT/US2009/057415, mailed Jan. 28, 2010, 8 pages.

International Search Report, Application No. PCT/US2009/061616, mailed Mar. 5, 2010, 8 pages.

Written Opinion for PCT/US2009/057408 dated Dec. 16, 2009 (7 pages).

Written Opinion for PCT/US2009/057415 dated Jan. 28, 2010 (7 pages).

Written Opinion for PCT/US2009/061616 dated Mar. 5, 2010 (7 pages).

International Preliminary Report on Patentability for PCT/US2009/057408 issued Mar. 29, 2011 (7 Pages).

International Preliminary Report on Patentability for PCT/US2009/057415 mailed Apr. 7, 2011 (8 Pages).

International Preliminary Report on Patentability for PCT/US2009/061616 issued May 3, 2011 (7 Pages).

* cited by examiner

METHODS AND DEVICES FOR DELIVERING AND APPLYING MULTIPLE SUTURE ANCHORS

FIELD OF THE INVENTION

The present invention relates to suture anchors and associated devices and methods for endoscopically suturing tissue.

BACKGROUND OF THE INVENTION

Endoscopic surgery, including procedures performed by way of endoscopic instruments such as gastroscopes, colonoscopes, laparoscopes, and the like, may be preferred as an alternative to open surgery due to the many advantages attributed to such "minimally invasive" techniques, such as shortened hospital stays, reduced recovery time, reduced risk of complications, and diminishment of the amount of and/or visibility of scarring caused by a surgical intervention. In many endoscopic procedures, as in open surgery, there are instances where a surgeon may desire to repair damaged or diseased tissues by apposing the tissues together using a suture. However, the suturing devices, stapling devices, and other fastener applicators that have been developed to aid surgeons performing open surgery generally cannot be easily redesigned to be passed through a flexible endoscopic instrument, which may have a working channel having an internal diameter in the range of about 2.0 to 4.0 millimeters. In addition, surgeons performing endoscopic procedures generally cannot simultaneously manipulate multiple devices fed through such working channels with sufficient ease to permit them to routinely emulate the "pass and catch" suturing techniques that may be employed in open surgery.

To address these problems, various suture anchors and applicator devices have been developed to permit surgeons to endoscopically emplace sutures within tissues. Such suture anchors may be deployed using applicator devices that are inserted within and extended through the working channel of an endoscope, carrying a suture anchor to the site of repair. The applicators typically include a cannulated needle portion which permits the surgeon to penetrate the tissues adjacent to diseased or damaged tissue and to deploy the suture anchor into the tissue to be apposed in a repair. The suture anchor is generally attached to a distal end of a suture, with the bulk of the suture extending alongside or within a portion of the applicator device and with a proximal end of the suture trailing outside the endoscopic instrument. The surgeon may deploy multiple suture anchors around the site of repair by serially passing multiple applicators through a flexible endoscope to the site of repair, or by repeatedly passing and withdrawing a single applicator that may be serially reloaded with additional suture anchors. The repeated insertion of each suture anchor and/or the repeated insertion, operation, and withdrawal of one or more endoscopic devices can increase the complexity of the endoscopic procedure as well as the complexity of equipment inventory and management within the operating environment.

Accordingly, there remains a need for methods and devices for deploying and applying multiple suture anchors without requiring repeated withdrawal of the device.

SUMMARY OF THE INVENTION

The present invention generally provides methods and devices for deploying and applying multiple suture anchors. In one embodiment, a surgical device is provided that includes an elongate shaft having a tissue-penetrating tip, a plurality of channels formed therein for seating a plurality of anchors, and an inner lumen extending therethrough for receiving suture extending from the plurality of anchors. The plurality of channels are configured such that upon insertion of the shaft through tissue an anchor can be selectively retracted relative to the shaft to engage tissue with a suture coupled thereto extending through the tissue. A distal portion of the shaft can have a plurality of openings formed in an outer surface thereof and in communication with the plurality of channels, and each of the plurality of openings can be configured to allow one of the plurality of anchors to be retracted therethrough.

The device can have any number of variations. For example, the shaft can be flexible such that the shaft can be passed through a tortuous pathway. As another example, the device can include a plurality of anchors, each anchor loaded in one of the plurality of channels. Each of the plurality of anchors can have a suture attached thereto, and each suture can optionally have a pushable knot formed thereon. As still another example, the device can include a plurality of suture channels formed in the shaft for seating suture extending proximally from a suture anchor, the plurality of suture channels being axially aligned with the plurality of channels. The plurality of channels can have a variety of configurations. For example, the plurality of channels can be arranged circumferentially around the inner lumen. The tissue-penetrating tip can also have a variety of configurations. For example, the tissue-penetrating tip can be formed on a penetrating element movably disposed in the inner lumen. In some embodiments, a distal end of the tissue-penetrating tip can be movable between a retracted configuration in which the distal end is contained within the inner lumen and a deployed position in which the distal end extends beyond an open distal end of the shaft. The tissue-penetrating tip can be rotatable relative to the shaft and/or can have a closed distal-most end.

In another embodiment, a surgical device is provided that includes an elongate flexible shaft and a plurality of suture anchors disposed within the shaft. Each suture anchor has a length of suture extending therefrom, and each of the plurality of suture anchors is configured to be deployed from the shaft through a sidewall of the shaft. The device can have a variety of configurations. For example, the sidewall of the shaft can have a plurality of openings, each of the plurality of suture anchors being configured to be deployed through one of the plurality of openings. For another example, each suture can be configured to be pulled to deploy one of the plurality of suture anchors coupled thereto. As yet another example, each suture can extend through a suture channel formed in the shaft. In some embodiments, the device can include a penetrating element movable through the shaft and having a tissue-penetrating tip rotatable relative to the shaft for penetrating tissue.

In other aspects, a surgical method is provided that includes inserting a tool through a tissue at a first location to position a plurality of pockets in a distal portion of the tool distally beyond the tissue, and pulling on a first suture to release a first suture anchor from one of the plurality of pockets. The method can have any number of variations. For example, prior to inserting the tool, the tool can be advanced through a working channel of an endoscope. As another example, inserting the tool can include rotating a penetrating element on a distal tip of the tool as the tool is advanced through the tissue. In some embodiments, the method can include, prior to inserting the tool, moving the penetrating element from a retracted position in which the penetrating element is fully contained within an elongate shaft of the tool to a deployed position in which at least a distal end of the penetrating element extends from a distal end of the elongate shaft. The method can also include inserting the tool through the tissue at a second location to position the plurality of pockets beyond the tissue, and pulling on a second suture to release a second suture anchor from one of the plurality of pockets. Prior to inserting the tool through the tissue at a second location, the tool can be removed from the tissue at the first location and remain within a body including the tissue for insertion at the second location. In some embodiments, the first and second sutures can extend through the tissue, and the method can include securing the first and second sutures to one another. Securing the first and second sutures can include advancing a knot formed on the first and second sutures. For another example, the method can include sterilizing the tool after at least one use.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for deploying and applying multiple suture anchors. In one embodiment, a surgical device is provided having a shaft configured to be introduced into a body, e.g., through a scoping device, and to deliver a plurality of suture anchors into tissue, preferably without the need to remove the shaft from the body. A person skilled in the art will appreciate that the term "tissue" as used herein is intended to encompass a variety of materials, e.g., organs, blood vessels, body lumens, and any other material that needs to be secured in a surgical procedure. A person skilled in the art will also appreciate that while the methods and devices are described in connection with endoscopic procedures in which the suture anchors are delivered through a natural orifice, the methods and devices disclosed herein can be used in numerous surgical procedures and with numerous surgical instruments. By way of non-limiting example, the devices can be used in laparoscopic procedures, in which the device is introduced percutaneously. The methods and devices can also be used in open surgical procedures. A person skilled in the art will also appreciate that the methods and devices disclosed herein can be used with any surgical tool, such as a scoping device, having a cannula or other working channel through which the shaft of a surgical instrument can be advanced and that is configured to be inserted into a body, such as through a natural orifice, through a puncture hole formed in tissue, and in any other way appreciated by a person skilled in the art. Non-limiting examples of a scoping device include an endoscope, a laparoscope, and a colonoscope. While the scoping device can be rigid or flexible, in an exemplary embodiment, the scoping device is flexible. Furthermore, the scoping device can be configured to pass through any portion of a body, but in an exemplary embodiment, the scoping device is configured to pass through a tortuous pathway. A person skilled in the art will appreciate that the term "tortuous pathway" as used herein is intended to include a tubular body lumen or organ, e.g., the colon or esophagus. Devices disclosed herein can alternatively or additionally be introduced into a body through an auxiliary passageway along the outside of a scoping device. One non-limiting example of a surgical instrument that provides such an auxiliary passageway can be found in commonly-owned U.S. Patent Publication No. 2004/0230095, which is hereby incorporated by reference in its entirety.

The devices discussed herein can be made from any combination of rigid and/or flexible materials, but in an exemplary embodiment the materials are biocompatible. A person skilled in the art will appreciate that the term "flexible" as used herein is intended to encompass a variety of configurations. Generally, a "flexible" member has some degree of elasticity, e.g., is capable of bending without breaking. In an exemplary embodiment, the device or at least portions thereof are composed of at least one biocompatible and flexible material, e.g., plastic, titanium, stainless steel, etc. Various portions of the device can also be formed from a shape memory material, such as Nitinol.

As indicated above, in an exemplary embodiment the device is configured to deliver a plurality of suture anchors to tissue. The suture anchors disposed in and deployable from the shaft can include any suture anchor having a suture attached thereto in any way appreciated by a person skilled in the art. The suture anchor can be configured to secure tissue with its attached suture, as will also be appreciated by a person skilled in the art. Each suture anchor disposed in the shaft can be the same or different from any one or more other suture anchors disposed in the shaft, but in an exemplary embodiment, each suture anchor disposed in the shaft is identical. Any size and shape of suture anchor can be used with the device. The suture anchor can be composed of any one or more materials as will be appreciated by a person skilled in the art, e.g., titanium, tantalum, stainless steel, a shape memory material, plastic, etc. In an exemplary embodiment, the suture anchor is composed of a rigid material such as stainless steel or titanium. The suture anchor can also have a fixed configuration, or expandable suture anchors can be used. For example, the suture anchor can be constrainable to a first configuration for deployment into tissue (e.g., when disposed in the shaft) and be expandable when unconstrained to a second configuration (e.g., when deployed from the shaft) for resisting pull-out from the tissue, such as when the suture anchor is composed of a shape memory material.

Figure 1:
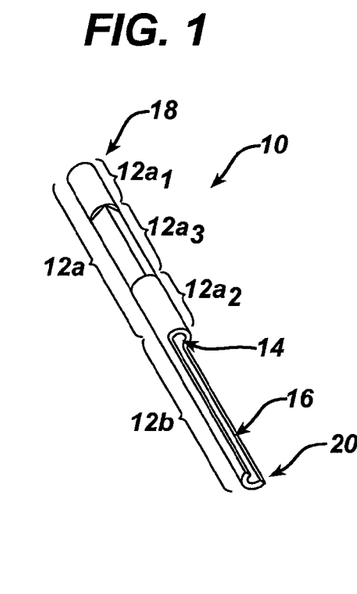
FIG. 1 is a perspective view of one embodiment of a suture anchor.
Figures 2, 3:
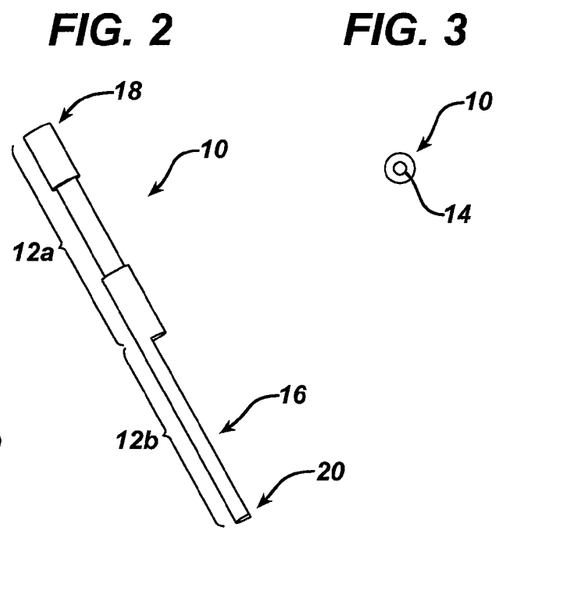
FIG. 2 is a side view of the suture anchor of FIG. 1.
FIG. 3 is an end view of the suture anchor of FIG. 1.

FIGS. 1-3 illustrate one exemplary embodiment of a suture anchor 10 that can be delivered and applied using the methods and devices described herein. The illustrated anchor 10 generally includes an elongate body that is configured to be positioned along a tissue surface, and that includes a suture coupled preferably to a mid-portion thereof. Such a configuration allows the elongate body to be inserted through tissue along the elongate body's longitudinal axis and then to pivot, e.g., about 90 degrees, to rest against and engage the tissue surface. The suture attached to the elongate body will extend through the tissue, thus allowing the suture to be used to reposition, tension, secure, or otherwise manipulate the tissue. While the elongate body can have various configurations, in an exemplary embodiment, the elongate body includes at least a portion that is configured to seat the suture to facilitate insertion of the suture anchor through tissue. In the illustrated embodiment, the elongate body has a first half, referred to herein as a cannulated portion 12a, and a second half in the form of a channeled portion 12b. The cannulated portion 12a can be substantially cylindrical along any or all portions of its length. As illustrated, outside surfaces of the proximal and distal regions 12a₁, 12a₂ of the cannulated portion 12a are substantially cylindrical while a mid-portion 12a₃ has a substantially rectangular cross-sectional shape. This rectangular cross-section can be the result of a crimp, applied to the cannulated portion 12a to keep a suture attached to the anchor 10 in place. The cannulated portion 12a has a lumen 14 extending therethrough that is in communication with a channel 16 in the channeled portion 12b. The channeled portion 12b can be substantially semi-cylindrical and can be formed from a cut-out section in the cannulated portion 12a. Although the cannulated and channeled portions 12a, 12b can have any size with respect to each other, a height of the channeled portion 12b can be approximately half the height of the cannulated portion 12a. In use, the channel 16 can be configured to seat the suture therein. In an exemplary embodiment, the lumen 14 and the channel 16 each have at least partially substantially circular cross-sections to help prevent a suture disposed therein from snagging on or otherwise being impeded by the anchor 10. FIG. 3 is an end view of the anchor 10 showing a substantially circular cross-section of the anchor 10 with the lumen 14 and the channel 16 extending therethrough between open terminal ends 18, 20 of the anchor 10. A person skilled in the art will appreciate that the cannulated portion 12a can be cannulated during manufacturing simply to facilitate formation of the channel 16 in the channeled portion 12b. In other embodiments, one or both of the suture anchor's terminal ends can be closed, and/or the suture anchor or portions thereof can be a solid member, e.g., without a passageway extending filly or partially therethrough.

Various other, non-limiting embodiments of suture anchors are described in commonly owned U.S. Patent Publication No. 2007/0112384, U.S. Patent Publication No. 2007/0112385, U.S. Patent Publication No. 2008/0161850, and U.S. Pat. No. 6,447,524, all of which are hereby incorporated by reference in their entireties.

As indicated above, the suture anchor 10 can also include a suture attached thereto, preferably at a mid-point thereof. Such a configuration can allow the anchor 10 to be deployed longitudinally through tissue and to pivot to engage the tissue. The suture can be any conventional surgical suture, as will be appreciated by a person skilled in the art. The suture can be composed of any material, e.g., cat gut, silk, polypropylene, polyester, stainless steel, etc., and the suture can have any shape and size, e.g., 2/0 suture, 3/0 suture, 4/0 suture, etc. The suture can be attached to the suture anchor in any way, as will be appreciated by a person skilled in the art. By way of non-limiting example, the suture can be crimped in a surface of the suture anchor, molded to the suture anchor, or knotted to the suture anchor. Non-limiting examples of various ways to attach a suture to a suture anchor are described in the above-mentioned U.S. Patent Publication Nos. 2007/0112384 and 2008/0161850.

Figure 4:
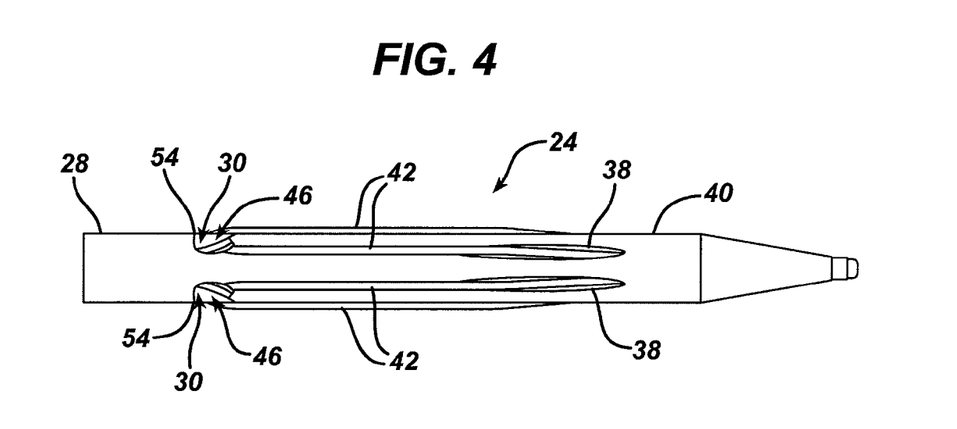
FIG. 4 is a side view of one embodiment of a surgical device configured to deliver and apply a plurality of suture anchors disposed therein.
Figure 5:
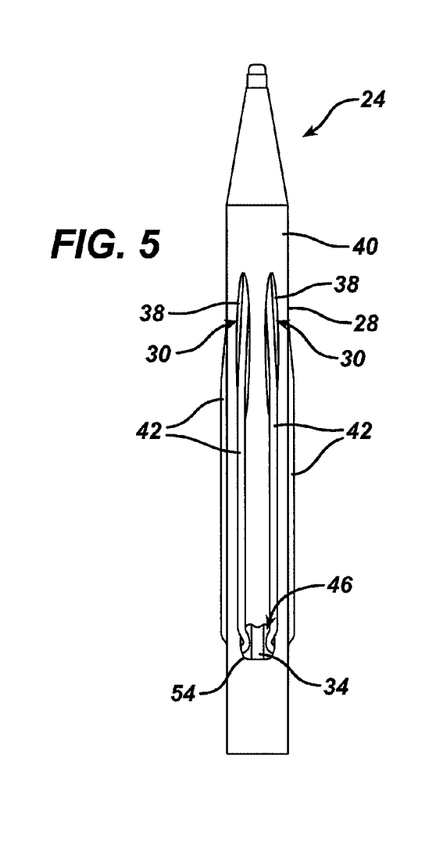
FIG. 5 is another side view of the device of FIG. 4 showing a plurality of suture anchors with sutures loaded in the device.

FIGS. 4-5 illustrate a surgical device 24 configured to deliver and apply at least one of a plurality of suture anchors to a tissue at a surgical site in a body of a patient. In an exemplary embodiment, the device 24 has an elongate shaft 28 that is flexible to allow it to be introduced into a body of a patient usually a minimally invasive technique, such as through a working channel of a flexible scoping device (or through an auxiliary channel of a flexible scoping device) having at least its distal end disposed in a body. The shaft 28 can be configured to have a plurality of suture anchors pre-loaded therein, such as the suture anchor 10 shown in FIGS. 1-3. Each of the suture anchors can be deployed from the shaft 28 sequentially and/or simultaneously with any number of the other suture anchors. In an exemplary embodiment, the shaft 28 can have a plurality of pockets or channels 30 for seating the plurality of sutures, and a plurality of anchor openings 38 formed in a sidewall 40 thereof. Each of the anchor openings 38 can be associated with at least one of the channels 30 such that a suture anchor can be deployed from the shaft 28 through the suture anchor's associated opening 38 in the shaft's sidewall 40. As discussed further below, each suture 42 attached to an anchor can exit the shaft 28 through its anchor's associated anchor opening 38 and can extend along and/or within the shaft 28 to a proximal end of the shaft 28. Pulling a proximal end of the suture 42 can deploy the suture's attached suture anchor from the shaft 28, e.g., through the suture anchor's associated anchor opening 38. In this way, multiple suture anchors disposed in the shaft 28 can be simultaneously introduced into a body and be selectively deployed from the shaft 28 in any number, in any order, and at any placement within the body as needed during a surgical procedure without the shaft 28 having to be removed from the body, thereby saving time and reducing chances of the shaft 28 introducing any unwanted fluid or tissue debris into the body and/or a cannula through which the shaft 28 is repeatedly introduced and removed from the body.

Figure 6:
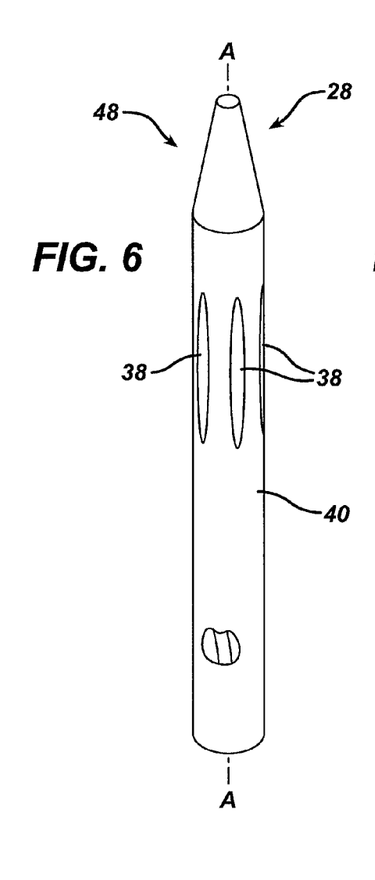
FIG. 6 is a perspective view of a shaft of the device of FIG. 4.
Figure 7:
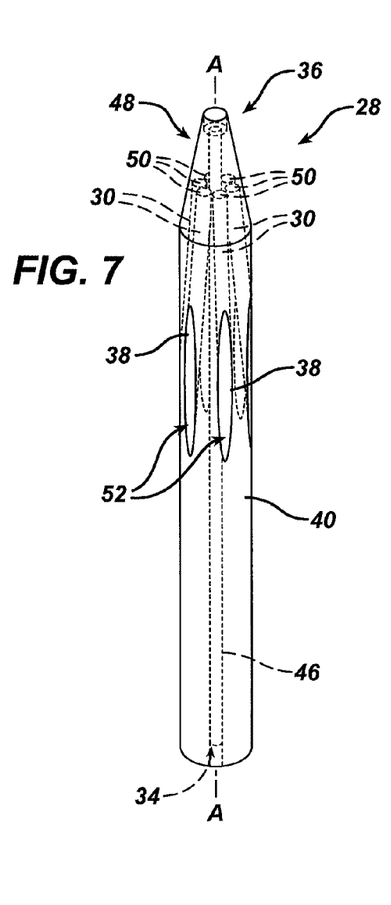
FIG. 7 is a partially transparent perspective view of a shaft of the device of FIG. 4.
Figure 8:
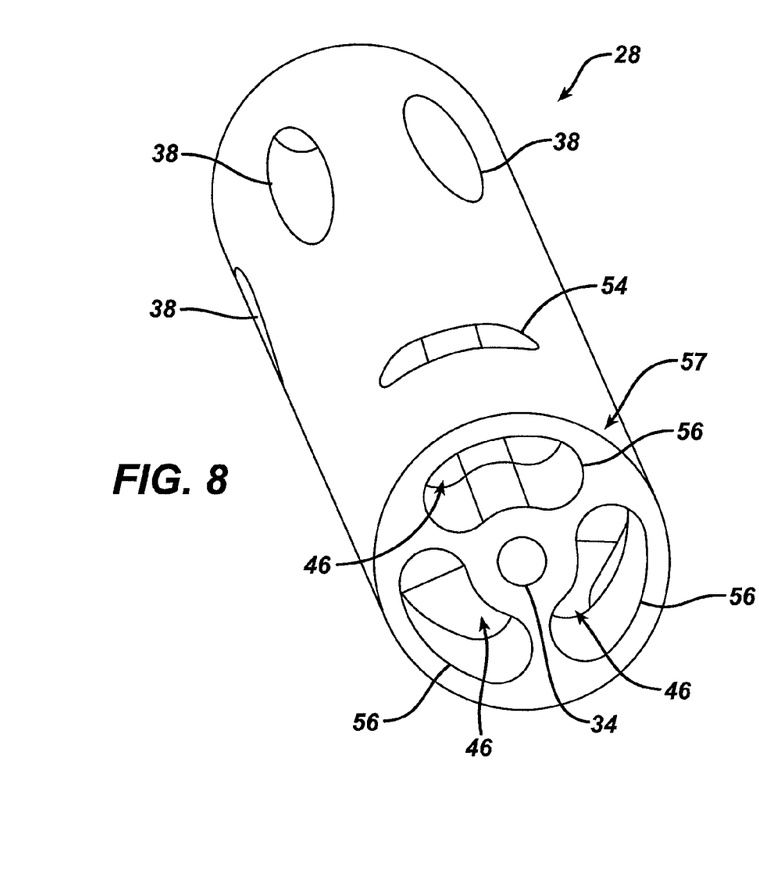
FIG. 8 is a perspective distal view of a shaft of the device of FIG. 4.
Figure 9:
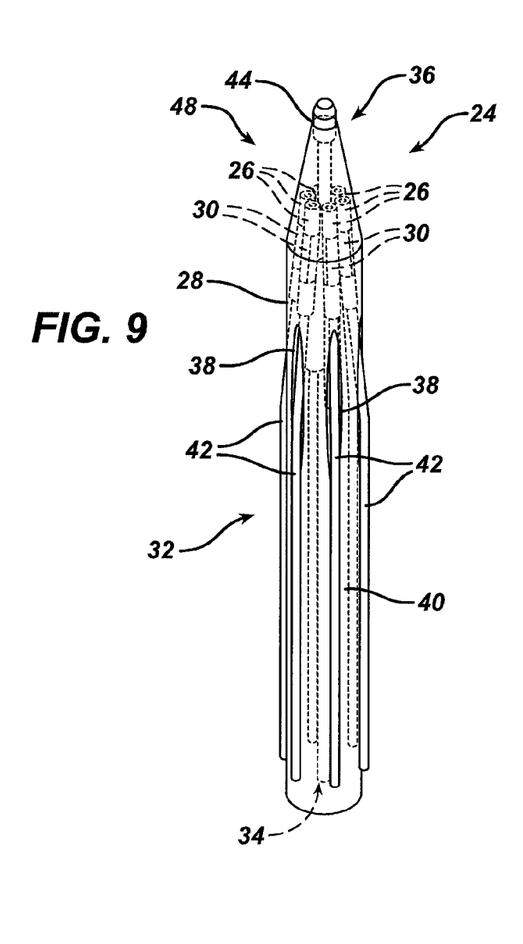
FIG. 9 is a partially transparent perspective view of the device of FIG. 4.
Figure 10:
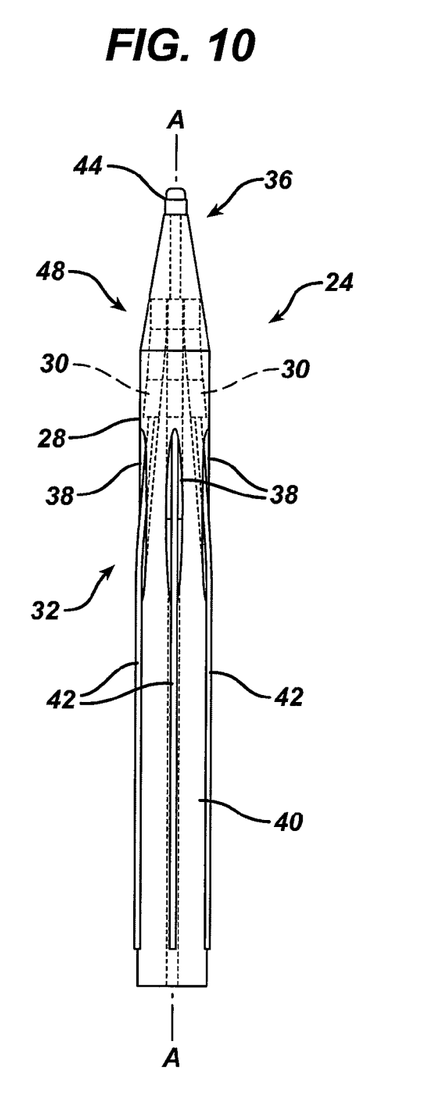
FIG. 10 is a partially transparent side view of the device of FIG. 4 showing a plurality of suture anchors with sutures loaded in the device.
Figure 11:
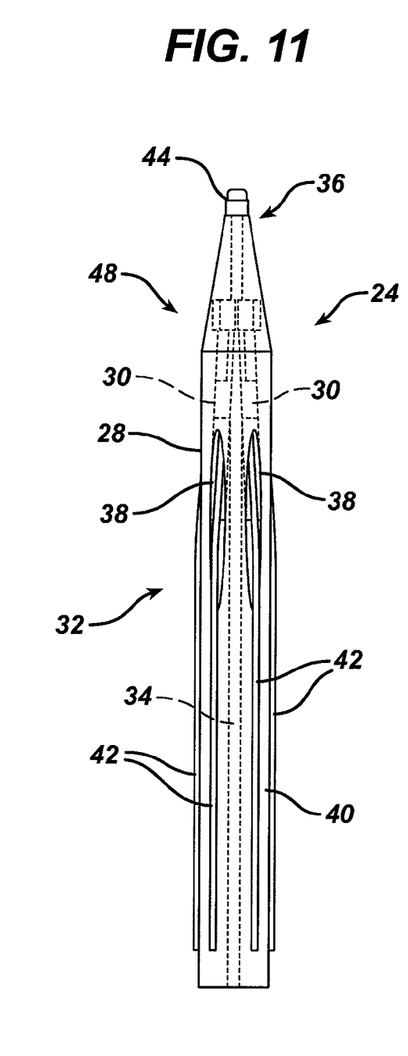
FIG. 11 is another partially transparent side view of the device and anchors of FIG. 10.
Figure 12:
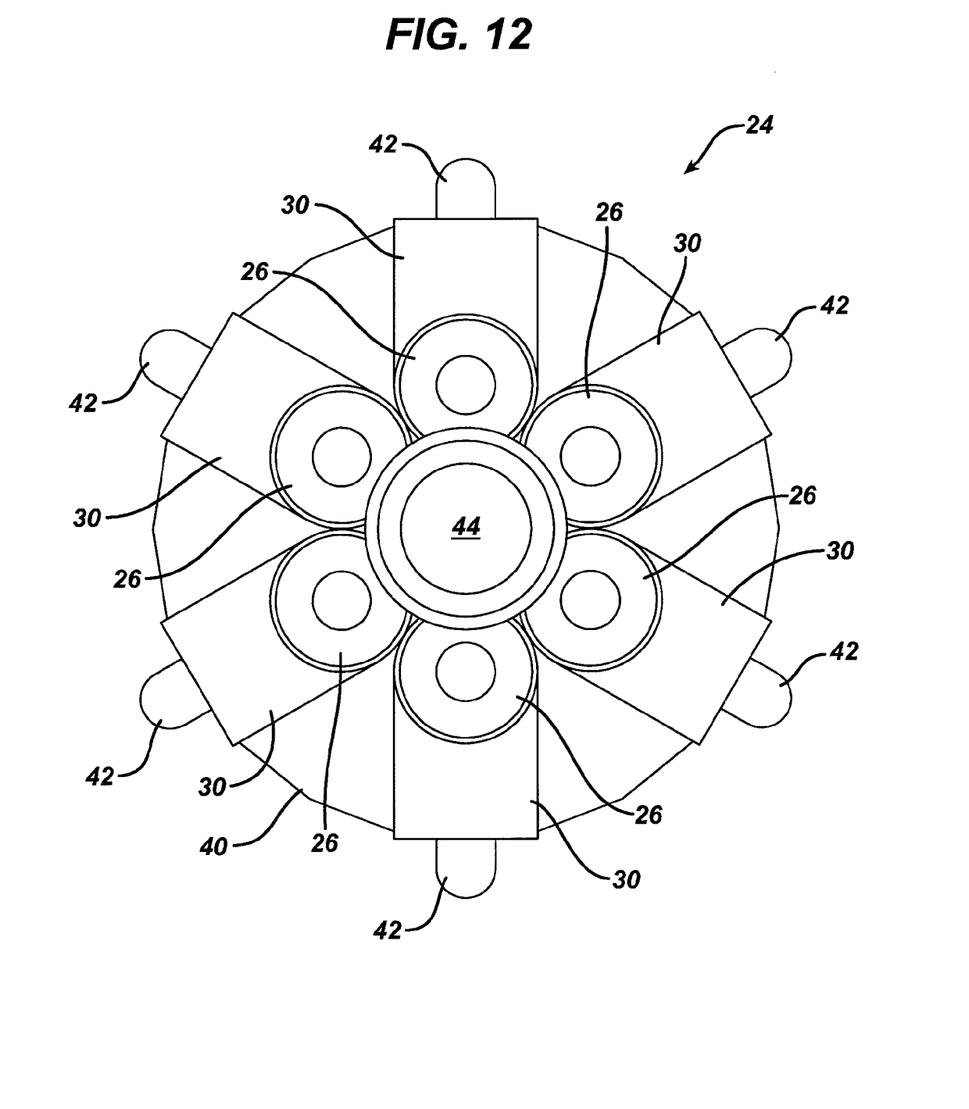
FIG. 12 is a partially transparent distal end view of the device of FIG. 4 showing a plurality of suture anchors with sutures loaded in the device.

The shaft 28, illustrated in FIGS. 6-8 as an independent element, can have a variety of configurations. The shaft 28 can be rigid, flexible, or a combination thereof, but it is preferably flexible at least along a substantial length thereof. Portions of the shaft's distal portion can be less flexible or more rigid than the remainder of the shaft 28 to facilitate insertion through tissue and/or anchor deployment. The shaft 28 can have any size, shape, and configuration. In an exemplary embodiment, the shaft 28 can be substantially cylindrical. The shaft 28 can have a uniform or non-uniform diameter along its longitudinal length. In an exemplary embodiment, a maximum diameter of the shaft 28 can be about 3.5 mm, which can allow the shaft 28 to be advanced through a device channel, natural orifice, body incision, etc. having a diameter greater than or equal to about 3.7 mm. Conventional scoping device working channels have a diameter of about 3.7 mm, and a shaft having a maximum diameter of about 3.5 mm can easily be disposed within the working channel. The shaft 28 can have a tapered nose 48, as illustrated, having a truncated-cone shape at its distal-most end, although the nose 48 can have another tapered shape, e.g., a cone shape, or not be tapered at all. A tapered nose 48 can help the shaft 28 more easily pass through tissue.

The shaft 28 can also include an inner lumen 34 extending therethrough between an at least partially open distal end 36 and an at least partially open proximal end 57. The inner lumen 34 can be configured to receive a penetrating element 44, discussed further below. The inner lumen 34 can be a cannulated tunnel having any size and shape, but the inner lumen 34 is preferably substantially cylindrical and preferably sized to receive the penetrating element 44 such that the penetrating element 44 can be slidably movable therein. The inner lumen 34 can be located anywhere within the shaft 28 but preferably extends along the shaft's central longitudinal axis A.

FIGS. 9-12 further illustrate the surgical device 24 and show the plurality of pockets or channels 30 formed in a distal portion 32 of the shaft 28. Each of the plurality of channels 30 can be configured to seat at least one of a plurality of suture anchors 26, as shown. The device 24 can include any number of channels 30 and any number of anchors 26, but in an exemplary embodiment, the channels 30 and the anchors 26 have a one-to-one relationship where a single channel is configured to seat a single anchor.

The pockets or channels 30 can each have any size, shape, and configuration. The channels 30 preferably each have a size and shape to seat the suture anchor desired to be seated within it and retracted therefrom. As illustrated, the channels 30 are each substantially elongate and cylindrical, but the channels 30 can have any shape, e.g., cone-shaped, truncated cone-shaped, rectangular, etc. In an exemplary embodiment, the channels 30 can each have a shape that complements and conforms to the shape of the suture anchor 10. The channels 30 can also be sized to retain the suture anchors 10, e.g., by interference or compression fit. While the channels 30 preferably each have identical size, shape, and configuration, the channels 30 can have different sizes, shapes, and/or configurations, e.g., if differently sized or shaped suture anchors are desired to be disposed in different one of the channels 30. Distal and proximal ends 50, 52 of the channels 30 can be open or closed in any combination. In an exemplary embodiment, however, the proximal ends 52 of the channels 30 are preferably open and in communication with at least one of the anchor openings 38 to allow anchors 26 disposed in the channels 30 to be proximally deployed from the channels 30, and the distal ends 50 of the channels 30 are preferably closed to help seat the anchors 26 therein and prevent them from distally moving out of the channels 30 and/or the shaft 28.

Figure 13:
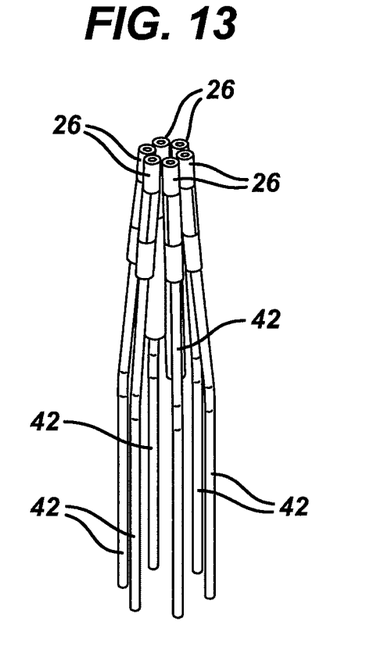
FIG. 13 is a perspective view of the suture anchors and sutures of the device of FIG. 10.

The channels 30 can generally extend longitudinally within the shaft 28, e.g., substantially parallel to a central longitudinal axis A of the shaft 28. Preferably, as best seen in FIGS. 6, 9, 10, and 12, and in FIG. 13 which shows the anchors 26 with attached sutures 42 configured to be positioned inside the channels 30 and the shaft 28, the channels 30 can be radially offset from and extend at an angle relative to the shaft's central longitudinal axis A, with distal ends 50 of the channels 30 being angled towards the longitudinal axis A and proximal ends being positioned further away from the longitudinal axis A. Such a distally-directed orientation of the channels 30 can allow the distal tip of the shaft 28 to be tapered for insertion through tissue and can help the anchors 26 disposed in the channels 30 be more easily removed therefrom when the anchors 26 are selectively deployed from the channels 30. The channels 30 can also be arranged in any way within the shaft 28, but, as shown, the channels 30 are preferably arranged circumferentially around the inner lumen 34. The channels 30 can be equidistantly spaced around the inner lumen's circumference, or there can be any other distance, same or different, between any adjacent channels. As shown in this embodiment, the six channels 30 are equidistantly spaced approximately sixty degrees apart from one another around the circumference of the inner lumen 34.

The anchor openings 38 that communicate with the channels 30 can also each have any size, shape, and configuration. The plurality of anchor openings 38 can be in communication with at least one of the channels 30, e.g., in a one-to-one relationship where a single opening is associated with a single channel. Preferably, the channels 30 and the anchor openings 38 generally have the same orientation with respect to the shaft 28, which can help in removing the anchors 26 from the shaft 28. The anchor openings 38 can thus be formed in and generally extend longitudinally along the shaft's sidewall 40 and can be substantially parallel to the shaft's longitudinal axis A. Also similar to the channels 30, the anchor openings 38 can be arranged in any way on the shaft 28, but, as shown, the anchor openings 38 are preferably arranged circumferentially and equidistantly around the shaft 28. As shown in this embodiment, the six anchor openings 38 are substantially elliptical and are equidistantly spaced approximately sixty degrees apart around the circumference of the sidewall 40. Each of the anchor openings 38 preferably have a size and shape to allow its associated one or more anchors 26 to be deployed through it. While the anchor openings 38 preferably each have identical size, shape, and configuration, the anchor openings 38 can each have a different size, shape, and/or configuration, e.g., if differently sized or shaped suture anchors are desired to be deployed through different ones of the anchor openings 38. The anchor openings 38 can generally maintain their size and shape, but any one or more of the anchor openings 38 can flex, e.g., if the shaft's sidewall 40 is composed of a flexible material.

In some embodiments, one or more of the anchor openings 38 can be configured to be substantially closed until (and if) one or more suture anchors are deployed through the one or more anchor openings 38, e.g., configured as slits, "doors," breakable members, etc. As slits, the anchor openings 38 can be configured as substantially longitudinal, flexible slots in the sidewall 40 which can flex open (including further open) when an anchor 26 disposed in the shaft 28 is pulled against an interior surface of the sidewall 40 to allow the anchor 26 to be pulled therethrough. As "doors," the anchor openings 38 can be configured as movable members, e.g., one or more hinged or springed flaps, having one-way motion such that pressure on an outside surface of a movable member does not cause any substantial movement of the movable member, but pressure on an inside surface of a movable member can cause the movable member to "open" like a door to allow an anchor 26 to exit the shaft 28 therethrough. As breakable members, the anchor openings 38 can include thinned or weakened regions in the sidewall 40 such that pressure on such a region of the sidewall 40 can "break" that portion of the sidewall 40 to allow an anchor 26 to be pulled therethrough. The thinned or weakened region(s) can be achieved by reducing the amount of material at that region, or by scoring or otherwise removing some of the material used to form the sidewall 40.

The shaft 28 can also include at least one suture opening 54 formed in its sidewall 40. The suture openings 54 can also each have any size, shape, and configuration. The suture openings 54 can be located proximal to and preferably axially aligned with the anchor openings 38 along the shaft's sidewall 40. There can be any longitudinal distance between the suture openings 54 and the anchor openings 38, but the distance is preferably minimized to reduce the amount of suture 42 exposed on an outside surface of the sidewall 40 to help prevent the suture 42 from tearing, snagging, or otherwise being damaged or interfering with any other structure during a surgical procedure. While the suture openings 54 preferably each have identical size, shape, and configuration, the suture openings 54 can each have a different size, shape, and/or configuration. The suture openings 54 can generally maintain their size and shape, but any one or more of the suture openings 54 can flex, e.g., if the shaft's sidewall 40 is composed of a flexible material. The suture openings 54 can be arranged in any way on the shaft 28, but, as shown, the suture openings 54 are preferably arranged circumferentially and equidistantly around the shaft 28. As shown, the suture openings 54 are substantially kidney-shaped and are equidistantly spaced around the circumference of the sidewall 40. The device 24 can include any number of suture openings 54, but in an exemplary embodiment, the suture openings 54 and the sutures 42 (and hence also the anchors 26) have at least a two-to-one relationship where a single suture opening is configured to have two (or more) sutures extending therethrough. In this way, each suture 42 extending through a single opening 54 can be more easily secured together following deployment of anchors 26 that need securing to tissue, as described further below. As illustrated, the device 24 includes three suture openings 54 spaced approximately one hundred twenty degrees apart around the shaft's circumference.

The sutures 42 can extend through the shaft 28 in the suture channels 46 and out the shaft's proximal end 57 where the sutures 42 can be pulled to deploy their respective anchors. The suture channels 46 can each have any size, shape, and configuration. While the suture channels 46 preferably each have identical size and shape and each extend longitudinally through the shaft 28 substantially parallel to the shaft's longitudinal axis A, the suture channels 46 can each have a different size, shape, and/or configuration, e.g., if differently sized sutures are used. Each of the sutures 42 can have its own dedicated suture channel 46 in the shaft 28 or, as shown, share a suture channel 46 with one or more other sutures 42 in the shaft 28.

In use, each of the anchors 26 can be removably seated in a channel 30 such that the anchors 26 can be removed from the device 10, preferably when at least the device's distal portion 32 is disposed in a body. As mentioned above, each of the sutures 42 can extend out of an anchor opening 38, along the shaft sidewall 40, and return into the shaft 28 through a suture opening 54 to extend through a suture channel 46 and out a proximal opening 56 to be accessible at the proximal end of the device 10. In an exemplary embodiment, each of the anchors 26 can be deployed from the shaft 28 by pulling its associated one of the sutures 42, thereby causing the anchor 26 attached to the pulled suture 42 to move proximally relative to the shaft 28 and be retracted from the channel 30 in which it is seated and exit the shaft 28 through the anchor's associated one of the anchor openings 38.

The anchors 26 disposed in the shaft 28 can be deployed from the shaft 28 in any order, generally at the option of the medical professional performing the surgical procedure. Moreover, as mentioned above, any number of the anchors 26 can be deployed during a single surgical procedure and can be deployed sequentially and/or simultaneously. The sutures 42 can be labeled, coded, or otherwise identified at their proximal ends to help a medical professional determine which of the sutures 42 are associated with adjacent anchors 26 and/or a shared suture opening 54. By non-limiting example, the sutures 42 can have a color coding at least at their proximal ends or can be threaded through labeled ports at the proximal end of the device 24. Preferably, if two or more of the anchors 26 are deployed to secure tissue in conjunction with each other, anchors 26 having sutures 42 passing through a shared suture opening 54, e.g., anchors 26 disposed adjacently around the circumference of the inner lumen 34, are preferably deployed to allow a securing element such as a pushable knot, e.g., a Roeder knot, to be advanced through the shared suture opening 54 to secure those sutures 42 and anchors 26. In an exemplary embodiment, the device 24 can include a plurality of pushable knots such that each pair of sutures 42 can have a pushable knot formed on their respective proximal ends, e.g., for a total of three pushable knots when the device 42 includes six anchors 26 and six sutures 42. Generally, sutures 42 can be considered associated with each other if they pass through the same suture opening 54. Following deployment of associated anchors 26, e.g., two anchors 26 having an associated pair of sutures 42, the pushable knot for those two sutures 42 can be pushed from the shaft 28 in any way, e.g., using a knot pusher device, as will be appreciated by a person skilled in the art. The pushable knot can be advanced through the suture channel 46 and exit the shaft 28 through the associated suture opening 54 to secure the knot against tissue, thereby securing the associated anchors 26 against tissue.

The device 24 can also include a securing element, e.g., a knotting element, a tying apparatus, etc., configured to secure two or more of the sutures 42 together following deployment of their respective anchors 26 to secure the deployed anchors 26 to tissue. For non-limiting example, a plurality of alternating right and left overhand knots can be applied using a knot pushing device or by applying a knotting element or other type of fastener, e.g., by way of a knotting element applicator advanced through a working channel or auxiliary channel of a scoping device. Various non-limiting embodiments of knotting elements are described in commonly owned U.S. Patent Publication No. 2007/0270889 and in PCT Patent Application No. PCT/US2008/062203 entitled "Loader for Knotting Element", which are hereby incorporated by reference in their entireties.

The device 24 can also include various other features, such as a handle at its proximal end to help guide the device 24 into a body, move the penetrating element 44 in the shaft 28, deploy the anchors 26, and/or perform any other functions as will be appreciated by a person skilled in the art. Any type of handle having any configuration can be used. Various non-limiting embodiments of handles are described in previously mentioned U.S. Patent Publication No. 2007/0112384 and in commonly owned U.S. Patent Publication No. 2008/0103527, which is hereby incorporated by reference in its entirety.

The shaft 28 can be inserted through tissue in a variety of ways, as will be appreciated by a person skilled in the art. For non-limiting example, a needle, a knife, or other cutting element can be introduced to the body through a scoping device, through the shaft 28, and/or in any other way appreciated by a person skilled in the art and can be used to cut tissue at a desired location. As shown in this exemplary embodiment, the penetrating element 44 can be used to penetrate tissue.

Figure 14:
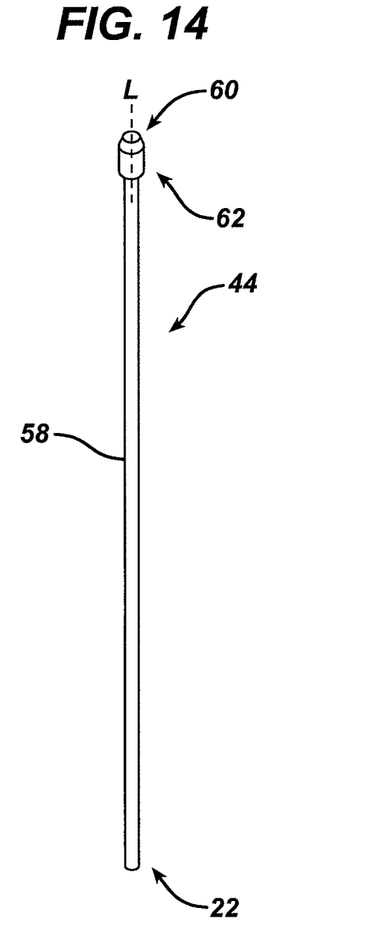
FIG. 14 is a perspective view of a tissue penetrating element of the device of FIG. 4.
Figure 15:
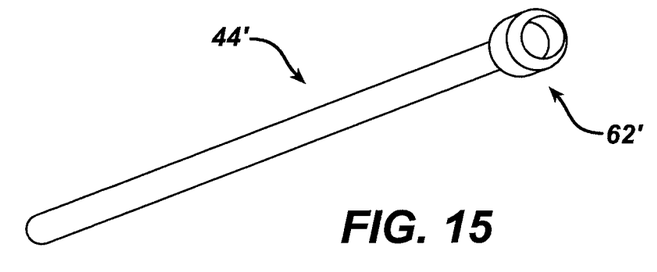
FIG. 15 is an alternate embodiment of a tissue penetrating element configured to be disposed in the device of FIG. 4.

The penetrating element 44, which is shown as an independent element in FIG. 14, can have a variety of shapes, sizes, and configurations. As illustrated, the penetrating element 44 can include an elongate shaft 58 having a cutting tip 60 at its distal end 62. The penetrating element's proximal end 22 can extend proximally beyond the shaft's proximal end 57 to allow the penetrating element 44 to be manipulated outside the body. Alternatively or in addition, a handle and/or controls can be disposed at the proximal end 22 to help manipulate the cutting tip 60, as will be appreciated by a person skilled in the art. The penetrating element 44 can have any shape, e.g., a substantially cylindrical shape, which can help the penetrating element 44 smoothly move through the inner lumen 34 of the shaft 28. Although the penetrating element's distal end 62 can have any shape, the distal end 62 is illustrated having a substantially cylindrical shape with a tapered cutting tip 60 configured to cut tissue. In other embodiments, the cutting tip 60 can include a beveled edge (including a chamfered edge), a pointed needle, an electronic cutter, etc. The penetrating element 44 can be composed any one or more flexible and/or rigid materials, although the penetrating element's shaft 58 is preferably flexible to allow it to be passed through a tortuous pathway while the tip 60 is preferably rigid, e.g., composed of stainless steel, titanium, etc., to help it cut tissue. The penetrating element 44 can be solid or can have one or more hollow portions. As a non-limiting example, FIG. 15 illustrates an alternative embodiment of a penetrating element 44' that includes an open distal end 62', as opposed to the closed distal end 62 shown in FIG. 14. A closed distal end can help prevent tissue or other body matter from entering the shaft 28 through the penetrating element 44, e.g., if tissue collection is not desired or a vacuum is not applied through the penetrating element 44.

As mentioned above, the penetrating element 44 can be movable, manually and/or electronically, within the shaft 28. The penetrating element 44 can be movable in any one or more ways, but in an exemplary embodiment, the penetrating element 44 is slidably and rotatably movable within the inner lumen 34 relative to the shaft 28. The penetrating element 44 can be slidably movable along to the device's longitudinal axis A such that the distal end 62 of the penetrating element 44 can be selectively contained within the shaft 28 and selectively extended beyond the shaft's distal end 36. In this way, the penetrating element's cutting tip 60 can be safely contained within the shaft 28 in a retracted position when desired, thereby preventing the tip 60 from cutting any undesired tissue (or any other undesired matter). When desired, the penetrating element 44 can be slidably advanced through the shaft 28 to a deployed position to extend at least the cutting tip 60 beyond the shaft's distal end 36 to allow the cutting tip 60 to cut tissue. FIGS. 4, 5, and 9-11 show the cutting tip 60 extending distally beyond the shaft's distal end 36. The device 24 can include a locking mechanism, e.g., a catch, a switch, etc., to lock the penetrating element 44 in place when the distal end 62 is contained within and/or extends beyond the shaft's distal end 36, as will be appreciated by a person skilled in the art.

The penetrating element 44 can cut tissue in any way, e.g., puncturing, slicing, etc., but as mentioned above, in an exemplary embodiment, the penetrating element 44 can rotate, which can allow the penetrating element 44 to cut tissue. Any or all portions of the penetrating element 44 can be rotatable, thereby allowing at least a portion of the distal end 62 to penetrate tissue and, if sufficiently rotated, causing an opening to form in the tissue. In an exemplary embodiment, the penetrating element's shaft 58 and distal end 62 including the cutting tip 60 can be rotatable relative to the device's shaft 28 such that rotating the penetrating element's shaft 58, e.g., from a proximal end of the device 24, can also rotate the cutting tip 60 at the distal end 62. At least a portion of the device 24, e.g., a portion of the shaft 28 including the anchor openings 38, can be advanced through the opening formed in the tissue by the penetrating element 44. Because the device 24 can deliver the penetrating element 44 to the tissue and can thus be located proximal to the opening when it is formed by rotation of the penetrating element 44, the device 24 can be advanced through the opening soon after the opening is formed, thereby helping to improve efficiency of the surgical procedure and reduce the surgical procedure's length. Using rotation to penetrate tissue instead of direct application of pressure, such as when puncturing tissue with a needle, can also help reduce risk of injuring tissue on the other side of the penetrated tissue.

Figure 16:
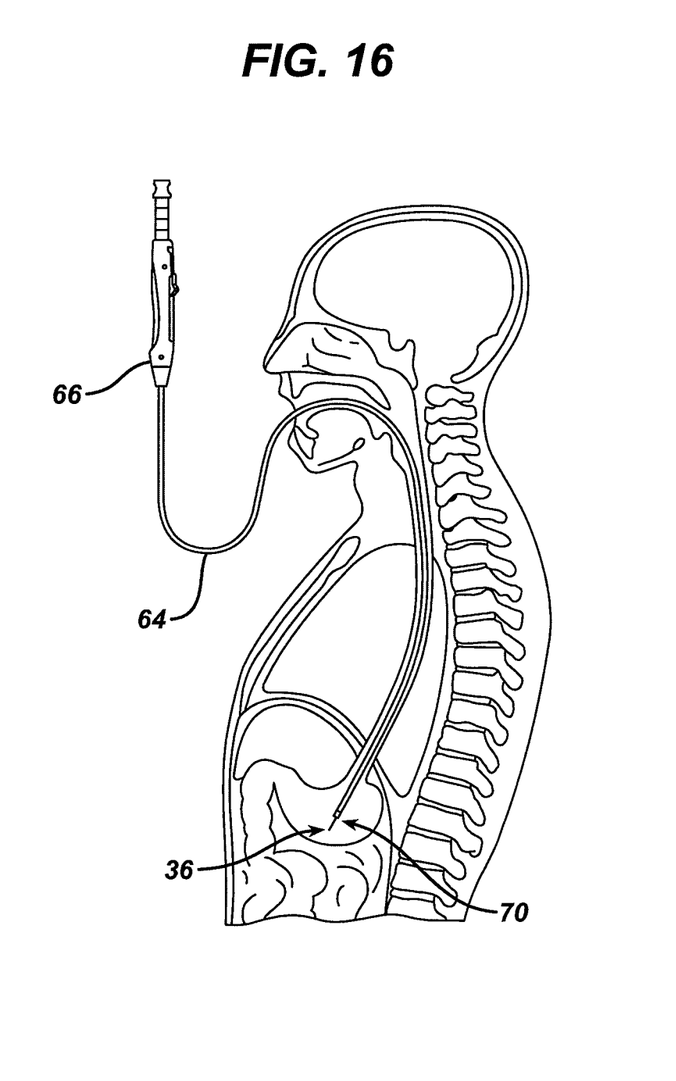
FIG. 16 is a schematic view of a flexible endoscope inserted into the upper gastrointestinal tract of a patient.

FIGS. 16-23 illustrate the device 24 in use in a minimally invasive surgical procedure to deliver and apply anchors 26 to a tissue of a patient. FIG. 16 illustrates a flexible endoscopic portion 64 of a scoping device, e.g., an endoscope 66, inserted into the upper gastrointestinal tract of a patient with the device 24 disposed therein with the device's distal end 36 extending beyond a distal end 70 of the endoscope 66. The device's distal end 36 is preferably delivered to a surgical site beyond the endoscope's distal end 70 through a working channel 68 of the endoscope 66 in a manner known to a person skilled in the art, e.g., by manipulating a proximal end of the shaft 28 extending outside a proximal end of the endoscope 66 after the endoscope's distal end 70 has been advanced to a desired location adjacent tissue, although the device 24 can be delivered to a surgical site in other ways and at any time during a surgical procedure. Although FIGS. 16-23 illustrate the use of the device 24 in an endoscopic procedure involving a system that includes the endoscope 66 having a working channel 68 through which the device 24 can be delivered to a surgical site, a person skilled in the art will appreciate that these and/or similar devices can be used in other ways in other types of surgical procedures. Furthermore, the tissue to which the anchor is attached can be any tissue, e.g., the stomach wall, the intestinal wall, the colon, etc.

Figure 17:
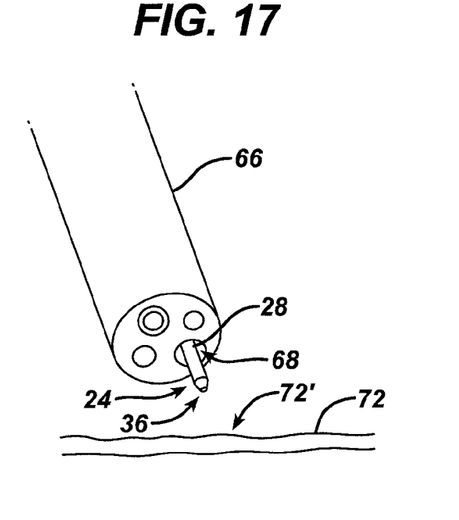
FIG. 17 is a side partially cross-sectional view of the device of FIG. 4 advanced through the endoscope of FIG. 16 and positioned adjacent to tissue.

As shown in FIG. 17, the distal end 36 of the device 24 with the anchors 26 disposed therein can be positioned near the tissue 72. The penetrating element 44 is not visible as it is in the retracted position and contained within the shaft 28, as it preferably also would be when positioned inside of the working channel 68 of the endoscope 66. The penetrating element 44 can be moved from its retracted position inside the shaft 28 to a deployed position where the cutting tip 60 of the penetrating element 44 is advanced beyond the endoscope's distal end 70. Any length of the penetrating element 44 and/or the shaft 28 can be advanced beyond the endoscope's distal end 70 in so positioning the cutting tip 60. The penetrating element 44, and more particularly the penetrating element's distal end 62, can be positioned at any angle with respect to a contact surface 72' of the tissue 72, although in an exemplary embodiment a longitudinal axis L of the penetrating element's distal end 62 (see FIG. 14) is substantially orthogonal to the contact surface 72' to help maximize the amount of rotational force applied to the tissue 72 upon rotation of the cutting tip 60 and to more quickly and easily penetrate the tissue 72.

Figure 18:
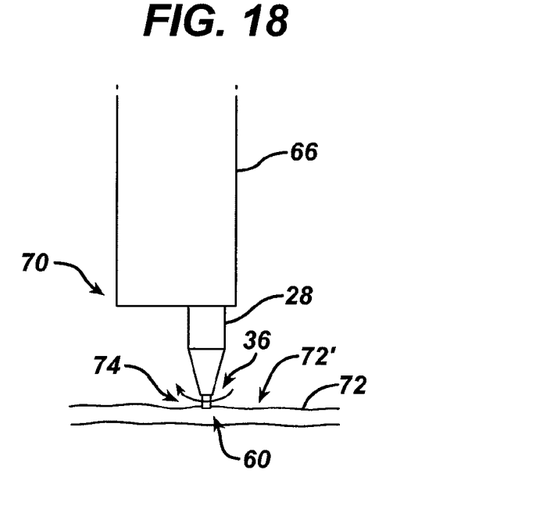
FIG. 18 is side partially cross-sectional view of the penetrating element of FIG. 14 being rotated in the device of FIG. 17 to penetrate through the tissue.

FIG. 18 shows the device 24 in a rotation position, e.g., rotating with the penetrating element 44 in the deployed position, where at least the cutting tip 60 of the penetrating element 44 extends beyond the device's distal end 36 and is being rotated with respect to the shaft 28 to begin to pierce into the tissue 72 at a first location 74. The cutting tip 60 (and any other portion of the penetrating element 44 being rotated) can be rotated any number of times, and can rotate in a clockwise and/or a counter-clockwise direction. The device's rotation, in combination with the tapered shape of the penetrating element's distal end 62 and/or with pushing the penetrating element 44 from its proximal end, can create or increase the size of an opening in the tissue 72. At least a portion of the penetrating element 44 can penetrate a portion of the tissue 72.

With the opening formed at the first location 74, the shaft 28 can be advanced through the tissue opening to effect a surgical procedure. Optionally, after the shaft 28 has been inserted through the tissue 72, the penetrating element 44 can be proximally moved into its retracted position where it is fully contained within the shaft 28 and the working channel 68, e.g., by pulling the penetrating element 44 from its proximal end. Alternatively or in addition, the opening can be maintained and/or increased by the use of other devices (not shown).

Figure 19:
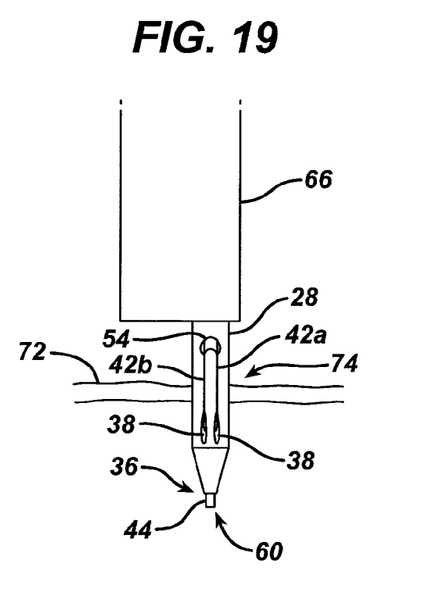
FIG. 19 is side partially cross-sectional view of the device advanced through the tissue of FIG. 18.

FIG. 19 shows the device 24 in an advanced position with its distal end 36 penetrated through the opening in the tissue 72 at the first location 74 created by the penetrating element 44 and entering the body cavity distal to the penetrated tissue 72. The cutting tip 60 of the penetrating element 44 still extends beyond the shaft's distal end 36, but the cutting tip 60 can be retracted into the shaft 28 at any time following its penetration through the tissue 72. FIG. 19 also shows the device 24 positioned in a pre-anchor-deployment position where the anchor openings 38 are positioned distal to the penetrated tissue wall 72. Such a pre-anchor-deployment position allows any of the anchors 26 to be deployed distal to the tissue wall 72 while allowing the deployed anchors' sutures 42 to pass through the tissue wall 72. In the pre-anchor-deployment position, the suture openings 54 can be positioned distal or proximal to the tissue wall 72, but the suture openings 54 are preferably positioned proximal to the tissue wall 72. The device 24 can optionally include a tissue stop, e.g., one or more protruding members located on an outside surface of the shaft 28 between the anchor openings 38 and the suture openings 54, to help limit the penetration depth of the device 24 through the tissue 72 and to help prevent injury to tissue on the distal, "blind" side of the tissue 72 being penetrated. Various tissue stops can be used as will be appreciated by a person skilled in the art, with non-limiting examples of a tissue stop described in previously mentioned U.S. Patent Publication No. 2007/0112385.

Figure 20:
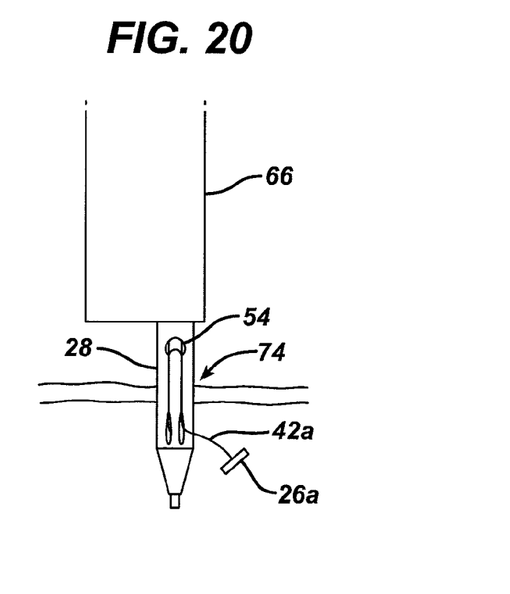
FIG. 20 is a side partially cross-sectional view of a first suture anchor deployed from the device of FIG. 19.

Once the anchors 26 are positioned beyond the tissue wall 72, one or more anchors 26 can be deployed from the shaft 28. Deployment can be achieved by applying tension to a suture 42 extending proximally from the proximal end of the shaft 28 to pull the anchor 26 attached thereto in a proximal direction, thereby pulling the anchor 26 out of the channel 30 and associated anchor opening 38. FIG. 20 shows one of the anchors, e.g., a first anchor 26a, deployed into the body cavity distal to the penetrated tissue 72, e.g., following pulling of the one of the sutures, e.g., a first suture 42a, attached to the deployed first anchor 26a. The first anchor's attached suture 42a extends therefrom and into the shaft 28 through one of the suture openings 54.

Figure 21:
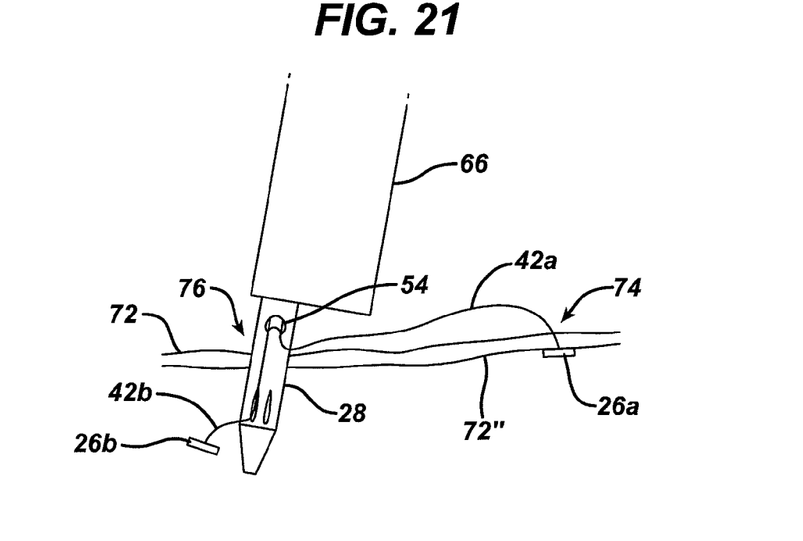
FIG. 21 is a side partially cross-sectional view of a second suture anchor deployed from the device of FIG. 20.

FIG. 21 shows the first deployed anchor 26a being drawn against a distal side 72" of the tissue 72 substantially at the first location 74 by, e.g., a tensile force being applied to its associated suture 42a. Since the suture 42a is attached to a mid-portion of the elongate body of the anchor 26a, the tensile force can cause the anchor 26a to pivot approximately 90 degrees to lie substantially parallel to the distal tissue surface 72", thereby engaging the tissue 72. FIG. 21 also shows the shaft 28 withdrawn from the first location 74 and advanced through the tissue 72 at a second location 76. The shaft 28 can be positioned adjacent the second location 76 and the penetrating element 44 can form an opening in the tissue 72 at the second location 76 similar to that described above for the first location 74. Also as shown in FIG. 21 and also similar to that described for the first deployed anchor 26a at the first location 74, another one of the anchors disposed in the shaft 28, e.g., a second anchor 26b, can be deployed from the shaft 28 by pulling on a suture, e.g., a second suture 42b, associated with the second anchor 26b. Deployment of the second anchor 26b can thus be achieved without removing the shaft 28 from the patient's body.

Figure 22:
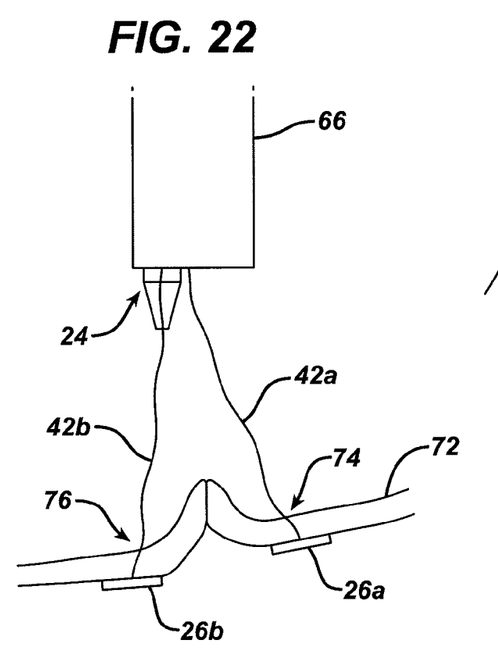
FIG. 22 is a side partially cross-sectional view of the deployed first and second suture anchors with sutures attached thereto and of the device removed from the tissue of FIG. 21.
Figure 23:
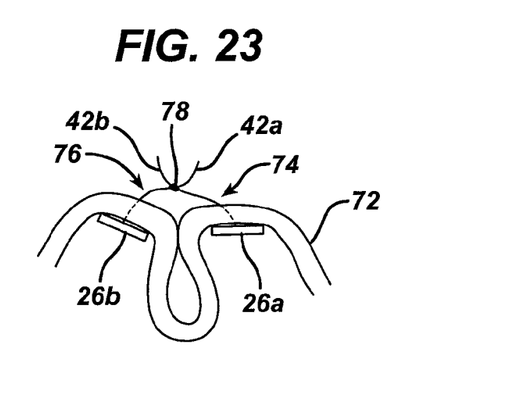
FIG. 23 is a side partially cross-sectional view of secured sutures attached to the deployed first and second suture anchors of FIG. 22.

FIG. 22 shows the first and second deployed anchors 26a, 26b being drawn against the distal side of the tissue 72 substantially at the first and second locations 74, 76, respectively. The first and second anchors 26a, 26b can be so moved by, e.g., applying a tensile force to their respective attached sutures 42a, 42b, thereby manipulating the anchors 26a, 26b and at least a portion of the tissue 72. FIG. 22 also shows the device 24, with the tissue penetrating element 44 retracted therein, being withdrawn from the tissue 72 and moving into the working channel 68. The sutures 42a, 42b attached to the deployed anchors 26a, 26b can extend through the tissue 72 substantially at the first and second locations 74, 76 and into the shaft 28 through the suture opening 54 associated with those two sutures 42a, 42b. The sutures 42a, 42b extending through the first and second locations 74, 76 can be secured together to help appose the tissue 72 using a securing element to help secure the first and second anchors 26a, 26b. As discussed above and as shown in FIG. 23, a pushable knot 78 at the proximal ends of the sutures 42a, 42b associated with the deployed anchors 26a, 26b can be pushed through its associated suture channel 46 in the device 24 and through the sutures' associated suture opening 54 to secure the anchors 26a, 26b as discussed above and as shown in FIG. 23. Alternately, the surgeon may thread the trailing ends of the sutures 42a, 42b through one of a number of types of knotting elements and associated knotting element applicators, feed the applicator through the flexible endoscope towards the apposed tissue 72, and "fire" the applicator to fix or "knot" the sutures 42 in place with the knotting element. The tissue 72 can thereby be drawn together substantially at the first and second locations 74, 76 to appose tissue between the first and second locations 74, 76. Any excess suture 42a, 42b can be trimmed near the knot 78, if desired, in any way, e.g., using an endoscopic cutting instrument, as will be appreciated by a person skilled in the art. One or both of the device 24 and the endoscope 66 can be removed from the surgical site and the patient's body at any point following sufficient securing of the tissue 72 and/or other tissue using any number of the anchors 26.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a plurality of anchors;
   a plurality of sutures, each of the plurality of anchors having one of the sutures coupled thereto; and
   an elongate shaft having a tissue-penetrating tip at a distal end thereof, a plurality of channels formed in the elongate shaft each configured to seat one of the plurality of anchors, and an inner lumen isolated from the plurality of channels and extending through the elongate shaft, the sutures each at least partially extending through the inner lumen, and the plurality of channels being configured such that upon insertion of the shaft through tissue each of the anchors can be selectively retracted proximally relative to the shaft by pulling the suture coupled thereto to release the anchor from the channel in which the anchor is seated and engage tissue with the suture coupled thereto extending through the tissue.

2. The device of claim 1, wherein a distal portion of the shaft has a plurality of openings formed in an outer surface thereof and in communication with the plurality of channels, each of the plurality of openings being configured to allow one of the plurality of anchors to be retracted therethrough.

3. The device of claim 2, wherein each of the openings is configured to move from a substantially closed configuration when its associated anchor is seated in its associated channel to an open configuration when its associated anchor is retracted therethrough.

4. The device of claim 1, wherein the plurality of channels are arranged circumferentially around the inner lumen.

5. The device of claim 1, wherein the tissue-penetrating tip is formed on a penetrating element movably disposed in the inner lumen.

6. The device of claim 5, wherein a distal end of the tissue-penetrating tip is movable between a retracted configuration in which the distal end is contained within the inner lumen and a deployed position in which the distal end extends beyond an open distal end of the shaft.

7. The device of claim 5, wherein the tissue-penetrating tip is rotatable relative to the shaft.

8. The device of claim 5, wherein the tissue-penetrating tip has a closed distal-most end.

9. The device of claim 1, wherein each of the anchors is loaded in one of the plurality of channels.

10. The device of claim 9, wherein each of the sutures has a pushable knot formed thereon.

11. The device of claim 1, wherein the shaft is flexible such that the shaft can be passed through a tortuous pathway.

12. The device of claim 1, further comprising a plurality of suture channels formed in the shaft configured to seat the sutures extending from the suture anchors, the plurality of suture channels being axially aligned with the plurality of channels.

13. The device of claim 1, wherein each of the anchors is configured to be deployed independent of a remainder of the anchors seated in the channels such that the anchors can be deployed sequentially from the shaft.

14. The device of claim 13, wherein the anchors are configured to be deployed simultaneously from the shaft.

15. The device of claim 1, wherein the plurality of channels are located entirely in a distal portion of the device.

16. The device of claim 1, wherein each of the plurality of channels has an open end and a closed end.

17. A surgical device, comprising:
   an elongate flexible shaft having proximal and distal ends;
   a handle at the proximal end of the elongate shaft; and
   a plurality of suture anchors disposed within a distal portion of the shaft, each suture anchor having a length of suture extending therefrom, each of the plurality of suture anchors being configured to be deployed from the shaft through a sidewall of the shaft, and each of the plurality of anchors being configured to be pulled proximally relative to the shaft to be deployed from the shaft through the sidewall of the shaft independent of a remainder of the anchors such that the anchors can be deployed sequentially from the shaft through the sidewall of the shaft,
   wherein each suture is configured to be pulled to deploy one of the plurality of suture anchors coupled thereto,
   wherein each suture extends through a suture channel formed in the shaft, and wherein a plurality of channels are formed in the elongate shaft each configured to seat one of the plurality of anchors, each of the plurality of channels having an open end and a closed end, where each of the plurality of channels are isolated from the suture channel.

18. The device of claim 17, wherein the sidewall of the shaft has a plurality of openings, each of the plurality of suture anchors being configured to be deployed through one of the plurality of openings.

19. The device of claim 17, further comprising a penetrating element movable through the shaft and having a tissue-penetrating tip rotatable relative to the shaft for penetrating tissue.

20. The device of claim 17, wherein the plurality of anchors are configured to be deployed simultaneously from the shaft.

21. The device of claim 17, wherein the elongate shaft has a tissue-penetrating tip at the distal end thereof.

22. The device of claim 17, wherein each of the plurality of anchors are configured to be pulled proximally relative to the shaft by pulling proximally the length of suture coupled thereto.

\* \* \* \* \*